(12) United States Patent
Liu et al.

(10) Patent No.: US 12,006,551 B1
(45) Date of Patent: Jun. 11, 2024

(54) MIRNA MARKER FOR DIAGNOSIS AND/OR TREATMENT OF ALZHEIMER'S DISEASE

(71) Applicant: INSTITUTE OF MEDICINAL BIOTECHNOLOGY, CHINESE ACADEMY OF MEDICAL SCIENCES AND PEKING UNION MEDICAL COLLEGE, Beijing (CN)

(72) Inventors: Rui Liu, Beijing (CN); Zhuorong Li, Beijing (CN); Li Zeng, Beijing (CN); Ting Sun, Beijing (CN); Mimin Liu, Beijing (CN); Junxia Zhang, Beijing (CN)

(73) Assignee: Institute of Medicinal Biotechnology, Chinese Academy of Medical Sciences and Peking University, Beijing (CN)

( * ) Notice: Subject to any disclaimer, the term of this patent is extended or adjusted under 35 U.S.C. 154(b) by 0 days.

(21) Appl. No.: 17/865,475

(22) Filed: Jul. 15, 2022

Related U.S. Application Data

(63) Continuation of application No. 17/614,414, filed as application No. PCT/CN2020/084626 on Apr. 14, 2020.

(30) Foreign Application Priority Data

Nov. 6, 2019 (CN) .......................... 201911078320.8

(51) Int. Cl.
- *C12Q 1/682* (2018.01)
- *C12Q 1/686* (2018.01)
- *C12Q 1/6883* (2018.01)

(52) U.S. Cl.
CPC .......... *C12Q 1/6883* (2013.01); *C12Q 1/686* (2013.01); *C12Q 2600/118* (2013.01); *C12Q 2600/16* (2013.01); *C12Q 2600/178* (2013.01)

(58) Field of Classification Search
CPC ..... A61P 25/28; C12N 15/113; C12Q 1/6883; C12Q 1/686; C12Q 260/118; C12Q 2600/178; C12Q 2600/16
See application file for complete search history.

(56) References Cited

U.S. PATENT DOCUMENTS

| | | | |
|---|---|---|---|
| 8,729,046 B2 * | 5/2014 | Rogler | A61K 31/07 536/23.1 |
| 10,138,520 B2 * | 11/2018 | Keller | C12Q 1/6883 |
| 10,844,380 B1 * | 11/2020 | Ryu | A61P 25/28 |
| 2005/0261218 A1 * | 11/2005 | Esau | C12N 15/111 536/23.1 |
| 2010/0279292 A1 * | 11/2010 | Marsh | A61P 35/00 435/375 |
| 2011/0003704 A1 * | 1/2011 | Skog | C12Q 1/6886 536/24.5 |
| 2013/0150428 A1 * | 6/2013 | Rogler | A61K 31/07 536/24.5 |
| 2017/0002348 A1 * | 1/2017 | Crary | C12Q 1/6883 |
| 2018/0023142 A1 * | 1/2018 | Weiner | A61P 21/02 435/6.12 |
| 2018/0275149 A1 * | 9/2018 | Clelland | A61K 31/19 |
| 2019/0249250 A1 * | 8/2019 | Bianco | C12Q 1/6883 |
| 2020/0392489 A1 * | 12/2020 | Ryu | A61P 25/28 |
| 2022/0259658 A1 * | 8/2022 | Liu | C12Q 1/6883 |

FOREIGN PATENT DOCUMENTS

| | | | | |
|---|---|---|---|---|
| CN | 105907842 | | 8/2016 | |
| CN | 110791560 | | 2/2020 | |
| CN | 110791560 A | * | 2/2020 | ............. A61K 45/00 |
| WO | WO-2007044937 A2 | * | 4/2007 | ........... C12N 15/113 |
| WO | WO-2011029903 A1 | * | 3/2011 | ........... A61K 31/713 |

OTHER PUBLICATIONS

Jiang et al., 2022. miR-23b-3p rescues cognition in Alzheimer's disease by reducing tau phosphorylation and apoptosis via GSK-3ß signaling pathways. Molecular Therapy-Nucleic Acids, 28, pp. 539-557. (Year: 2022).*
Lee et al., Dec. 1, 2021. miRNAs as therapeutic tools in Alzheimer's disease. International Journal of Molecular Sciences, 22(23), 13012, pp. 1-14. (Year: 2021).*
Martinez, B. and Peplow, P.V., Feb. 2019. MicroRNAs as diagnostic and therapeutic tools for Alzheimer's disease: advances and limitations. Neural regeneration research, 14(2), p. 242-255. (Year: 2019).*
Pan et al., 2021. MicroRNA-23b attenuates tau pathology and inhibits oxidative stress by targeting GnT-III in Alzheimer's disease. Neuropharmacology, 196, 108671, pp. 1-10. (Year: 2021).*
Reddy et al., 2017. A critical evaluation of neuroprotective and neurodegenerative MicroRNAs in Alzheimer's disease. Biochemical and Biophysical Research Communications, 483(4), pp. 1156-1165. (Year: 2017).*
Ryan et al., Oct. 2018. Circulating plasma microRNAs are altered with amyloidosis in a mouse model of Alzheimer's disease. Journal of Alzheimer's Disease, 66(2), pp. 835-852. (Year: 2018).*
Shaik et al., 2018. The role of microRNAs in Alzheimer's disease and their therapeutic potentials. Genes, 9(4), 174, pp. 1-36. (Year: 2018).*

(Continued)

*Primary Examiner* — Gary Benzion
*Assistant Examiner* — Olayinka A Oyeyemi
(74) *Attorney, Agent, or Firm* — Jerold I. Schneider; Schneider IP Law

(57) ABSTRACT

A miRNA marker for the treatment and/or diagnosis of Alzheimer's disease (AD), and the miRNA marker is a miRNA23 cluster. The miRNA23 cluster is used in the diagnosis and treatment of AD. The expression of the miRNA23 cluster is detected using primers for the microRNA marker through AD model cells, AD model animals and natural aging animals, and blood of AD patients, and it is found that the expression of the miRNA23 cluster is significantly reduced during the progression of AD, which reduces neuronal apoptosis by inhibiting the GSK-3β-mediated tau protein phosphorylation. Therefore, the miRNA23 cluster can be used as a novel biomarker and therapeutic target for the early, non-invasive diagnosis and treatment of AD.

1 Claim, 8 Drawing Sheets
Specification includes a Sequence Listing.

(56) References Cited

OTHER PUBLICATIONS

Wang et al., 2017. Profiling microRNA from brain by microarray in a transgenic mouse model of Alzheimer's disease. BioMed Research International, 2017, vol. 2017, Article ID 8030369, pp. 1-11. (Year: 2017).*

Chen et al., 2014. MicroRNA-23a/b and microRNA-27a/b suppress Apaf-1 protein and alleviate hypoxia-induced neuronal apoptosis. Cell death & disease, 5(3) e1132, pp. 1-12. (Year: 2014).*

Liu et al., 2014. Identification of microRNAs involved in Alzheimer's progression using a rabbit model of the disease. American journal of neurodegenerative disease, 3(1), p. 33-44. (Year: 2014).*

Martinez et al., 2019. MicroRNAs as diagnostic and therapeutic tools for Alzheimer's disease: advances and limitations. Neural regeneration research, 14(2), p. 242-255. (Year: 2019).*

Sun et al., 2018. miR-23b improves cognitive impairments in traumatic brain injury by targeting ATG12-mediated neuronal autophagy. Behavioural brain research, 340, pp. 126-136. (Year: 2018).*

Weinberg et al., 2015. Evidence for a neuroprotective microRNA pathway in amnestic mild cognitive impairment. Frontiers in neuroscience, 9, p. 430.Front. Neurosci., 9 (2015), 430, pp. 1-12. (Year: 2015).*

English Description of CN110791560, publishe Feb. 14, 2020. pp. 1-7 (Year: 2020).*

Weinberg et al "Evidence for a neuroprotective microRNA in amnestie mild cognitive impairment", Frontiers in Neuroscience 9:430; Nov. 5, 2015.

Luigi et al "Plasma Exosomal miRNA in Persons with and without Alzheimer Disease:Altered Expression and Prospects for Biomarkers" PLoS ONE 10(1); Oct. 1, 2015.

ISR for PCT / CN2020/084626.

* cited by examiner

MIRNA MARKER FOR DIAGNOSIS AND/OR TREATMENT OF ALZHEIMER'S DISEASE

CROSS-REFERENCE TO RELATED APPLICATIONS

This patent application is a continuation of U.S. application Ser. No. 17/614,414 filed on Nov. 21, 2021, which application Ser. No. 17/614,141 is the U.S. 371 entry of application PCT/CN2020/084626 filed on Apr. 14, 2020, and which claims the benefit and priority of Chinese Patent Application No. 201911078320.8, filed on Nov. 6, 2019, with the name "miRNA marker for diagnosis and/or treatment of alzheimer's disease." The disclosures of each of the three listed applications is incorporated by reference herein in its entirety as part of the present application, and the benefit of priority of each of the three listed applications is hereby claimed.

TECHNICAL FIELD

The disclosure relates to the field of biotechnology, and in particular, to the use of a microRNA (miRNA for short) marker for diagnosing and/or treating Alzheimer's disease (AD).

BACKGROUND

At present, Alzheimer's disease (AD) is defined as a neurodegenerative disease with senile plaques, neurofibrillary tangles, and neuron loss as main pathological features, which is mainly characterized by progressive memory impairment, cognitive impairment, and neuropsychiatric symptoms such as personality changes and language disorders. Existing studies have shown that amyloid-beta peptide (AD) hypothesis, tau protein hyperphosphorylation hypothesis, and cholinergic imbalance hypothesis are the main pathogenetic theories in the pathological process of AD, and most of the drugs currently in clinical research are also based on the above hypotheses. At present, there are mainly the following problems in the prevention and treatment of AD: lack of non-invasive and early diagnostic biomarkers, unclear pathological mechanisms, and lack of credible drug targets. Therefore, seeking reliable diagnostic markers for AD and elucidating the pathogenesis of AD are scientific problems that need to be solved urgently in the prevention and treatment of AD so far. Studies have shown that familial Alzheimer's disease (FAD) involves mutation of genes such as PSEN1, PSEN2, and APP, which can be found through early genetic screening. However, specific pathogenic genes associated with sporadic Alzheimer's disease (SAD) have not been reported so far, and patients with SAD account for 95% of the total AD patients. In the study of SAD, targeting disease-modified specific functional genes is of great significance for the prevention, treatment, and discovery of clinical biomarkers in AD.

SUMMARY

To this end, the examples of the disclosure provide a miRNA marker for the diagnosis of AD to solve the problem that there is no diagnostic marker for AD at the gene level at present.

To achieve the foregoing objective, the examples of the disclosure provide the following technical solutions:

The disclosure provides a miRNA marker for diagnosing and/or treating AD, and the miRNA marker is a miRNA23 cluster.

Preferably, the miRNA23 cluster is selected from hsa-miR-23b, with a nucleotide sequence shown in SEQ ID NO. 1;

the miRNA23 cluster is selected from hsa-miR-23b-3p, with a nucleotide sequence shown in SEQ ID NO. 2.

The examples of the disclosure further provide use of a primer in the preparation of a kit, and the primer is a primer specific for the miRNA marker described above.

Preferably, the kit is used to diagnose AD, predict the risk of developing AD, or predict the outcome of AD in patients suffering from or at risk of developing AD.

Preferably, the primer is used to determine the expression level of the miRNA marker in a sample.

Preferably, the sample is serum.

Preferably, the expression level of the miRNA marker is based on the expression level of the miRNA marker in a patient and the reference expression level of the miRNA marker in a healthy subject.

Preferably, the expression level of the miRNA marker is determined by a sequencing-based method, an array-based method, or a PCR-based method.

The examples of the disclosure further provide use of an agonist for the miRNA marker described above in the preparation of a medicament for treating AD.

In an example of the disclosure, the expression of the microRNA of miRNA23 cluster is reduced during AD, which inhibits the GSK-30-mediated tau protein phosphorylation to reduce the apoptosis of neuronal cells. The miRNA of miRNA23 cluster is:

(1) The miRNA23 cluster is selected from the following:
  (a) classification of microRNAs, where, the miRNA 23b is selected from hsa-miR-23b, with a sequence shown in SEQ ID NO. 1: cucaggugcucuggcugcuugg-guuccuggcaugcugauuugugacuuaagauuaaaauca-cauugccag ggauuaccacgcaaccacgaccuuggc, and the default mature body (hsa-miR-23b-3p) thereof has a sequence shown in SEQ ID NO. 2: aucacauugccagg-gauuaccac; and (b) modified derivatives of microRNAs; or microRNAs or modified miRNA derivatives with the same or substantially the same functions as microRNAs length of 18 nt to 26 nt.

The examples of the disclosure provide a preparation and a medicament, which are agonists for the microRNA in (1).

The examples of the disclosure have the following advantages:

The examples of the disclosure show that the miRNA23 cluster plays a role in the diagnosis and treatment of AD. The expression of the miRNA23 cluster is detected using primers and/or probes for the microRNA marker through AD model cells, AD model animals and natural aging animals, and blood samples of AD patients, and it is found that the expression of the miRNA23 cluster is significantly reduced during the progression of AD. Therefore, the miRNA23 cluster can be used as a novel AD marker for the early diagnosis of AD. The examples of the disclosure show that the up-regulation of miRNA23 cluster decreases the expression of GSK-30, inhibits the tau protein phosphorylation, and reduces neuronal apoptosis; the down-regulation of miRNA23 cluster increases the tau protein phosphorylation level and promotes the neuronal apoptosis; the miRNA23 cluster exerts the neuroprotective effect by down-regulating the expression of GSK-3β during the progression of AD. Collectively, the examples of the disclosure reveal the functions of the miRNA23 cluster in AD. Based on the above findings, the miRNA23 cluster can be used as a new therapeutic target and an early non-invasive diagnostic biomarker for AD, which provides a new idea and technique for the specific-target therapy using the miRNA23 cluster.

BRIEF DESCRIPTION OF DRAWINGS

In order to more clearly illustrate the implementations of the disclosure or the technical solutions in the prior art, the following will briefly introduce the figures that need to be used in the description of the implementations or the prior art. It should be noted that these figures in the following description only give typical examples, and other implementation figures can be derived from the provided figures without creative work for ordinary skill in the art.

DETAILED DESCRIPTION

Figure 1:
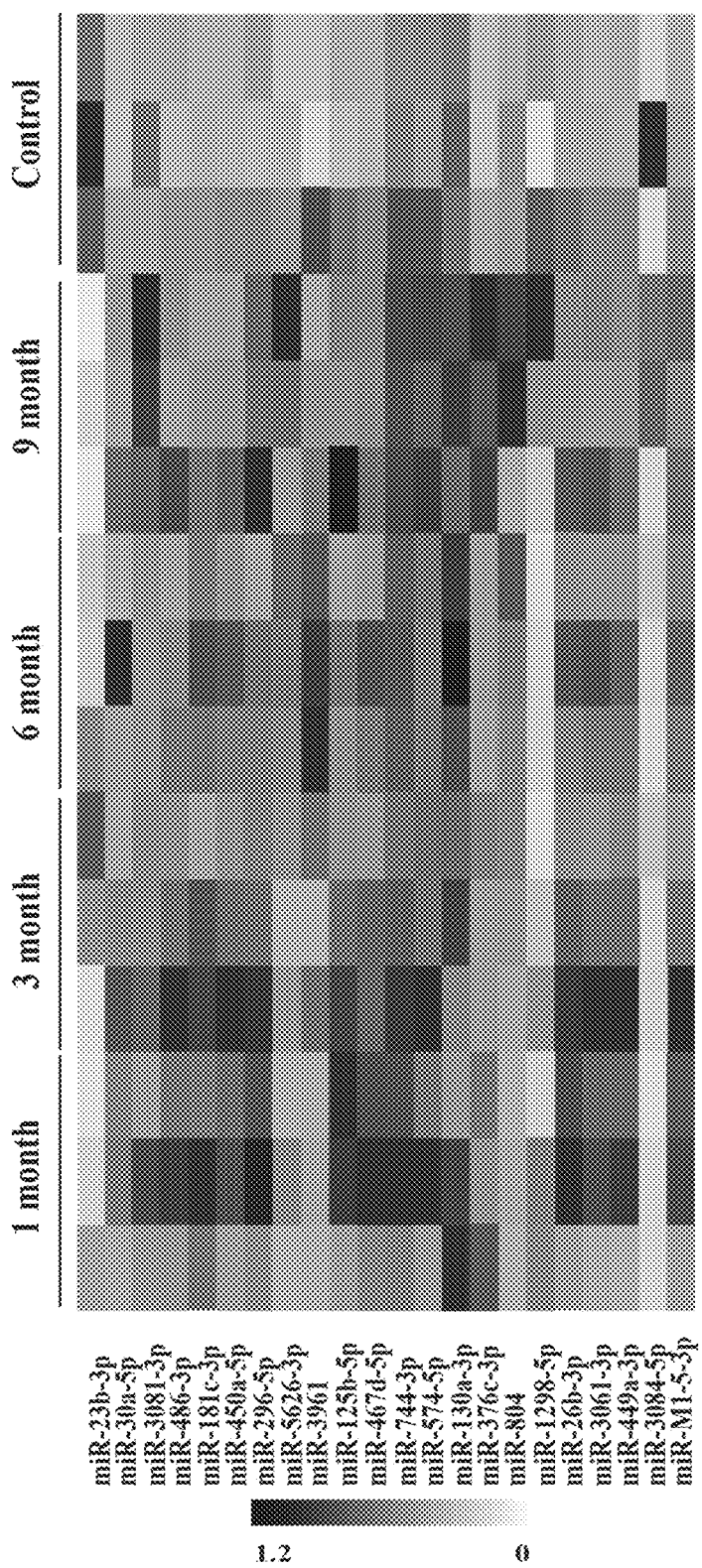
FIG. 1 shows the continuously decreased miR-23b expressions in brain tissues of AD model animals detected by miRNA microarray according to a specific example of the disclosure.

The implementation of the disclosure will be illustrated below in conjunction with specific examples. Those skilled in the art can easily understand other advantages and effects of the disclosure from the content disclosed in this specification. Obviously, the described examples are merely a part rather than all of the examples of the disclosure. All other examples obtained by a person of ordinary skill in the art based on the examples of the disclosure without creative efforts shall fall within the protection scope of the disclosure.

In the examples of the disclosure, the term "expression level" refers to a measured expression level compared with a reference nucleic acid (for example, from a control), or a calculated average expression value (for example, in RNA microarray analysis). A specified "expression level" can also be used as a result and determined by the comparison and measurement of a plurality of nucleic acids of interest disclosed below, and show the relative abundance of these transcripts with each other. The expression level can also be evaluated relative to the expression of different tissues, patients versus healthy controls, etc.

In the context of the disclosure, a "sample" or "biological sample" is a sample that is derived from or has been in contact with a biological organism. Examples of biological samples are cells, tissues, body fluids, biopsy samples, blood, urine, saliva, sputum, plasma, serum, cell culture supernatant, etc.

A "gene" is a nucleic acid segment that carries the information necessary to produce a functional RNA product in a controlled manner. A "gene product" is a biomolecule produced by gene transcription or expression, such as mRNA or translated protein.

"miRNA" is a short, naturally occurring RNA molecule and should have the general meaning understood by those skilled in the art. A "miRNA-derived molecule" is a molecule obtained from a miRNA template chemically or enzymatically, such as cDNA.

In the examples of the disclosure, the term "array" refers to an arrangement of addressable positions on a device (such as a chip device). The number of locations can vary from a few to at least hundreds or thousands. Each position represents an independent reaction site. Arrays include, but are not limited to, nucleic acid arrays, protein arrays, and antibody arrays. "Nucleic acid array" refers to an array including nucleic acid probes, such as oligonucleotides, polynucleotides, or large portions of genes. The nucleic acids on the array are preferably single-stranded.

"PCR-based method" refers to a method involving polymerase chain reaction (PCR). This is a method of exponentially amplifying nucleic acids "such as DNA or RNA" using one, two or more primers to replicate enzymatically in vitro. For RNA amplification, reverse transcription can be used as the first step. PCR-based methods include kinetic or quantitative PCR (qPCR), particularly suitable for analyzing expression levels. When it achieves the determination of the expression level, for example, a PCR-based method can be used to detect the presence of a given mRNA, which reverse transcribes a complete mRNA library (the so-called transcriptome) into cDNA with the help of reverse transcriptase. The presence of a given cDNA is detected with the help of corresponding primers. This method is commonly referred to as reverse transcriptase PCR (RT-PCR).

In the examples of the disclosure, the term "PCR-based method" includes both end-point PCR applications and kinetic/real-time PCR techniques using special fluorophores or intercalating dyes, which emit fluorescent signals as functions of amplification targets and allow monitoring and quantification of the targets.

In the examples of the disclosure, the term "marker" or "biomarker" refers to a biomolecule whose presence or concentration can be detected and associated with known conditions (such as a disease state) or clinical outcomes (such as response to treatment), such as nucleic acids, peptides, proteins, and hormones.

Example 1 Detection of Aberrant Expression of miR-23b in Brain Tissues of AD Model Animals and WT Animals Using Microarray 1, 3, 6, and 9-month-old APP/PS1 double-transgenic mice were selected, RNA was extracted from the brain tissues of the mice, and miRNA was labeled. The miRNA of miRNA23 cluster in the examples of the disclosure was hsa-miR-23b, with a sequence shown in SEQ ID NO. 1: cucaggugcucuggcugcuugggguuccuggcaugcugauuugugac- uuaa gauuaaaaucacauugccagggauuaccacgcaaccacgaccuuggc. The default mature body (hsa-miR-23b-3p) thereof had a sequence shown in SEQ ID NO. 2: aucacauugccagg-gauuaccac. The mature body (hsa-miR-23b-3p) miRNA involved: reverse transcription primer: SEQ ID NO. 3: gtcgtatcca gtgcagggtc cgaggtattcgcactggatacgacgtggta; quantitative PCR (qPCR) forward primer: SEQ ID NO. 4: cgatcacattgccagggat; and reverse primer: SEQ ID NO. 5: agtgcagggtccgaggtatt. Then the sample was hybridized on the miRCURYTM LNA Array (v.18.0). A microarray was scanned with Axon GenePix 4000B microarray scanner, and the original data were analyzed using GenePix pro V6.0 software. As shown in FIG. 1, compared with WT mice, the expression of miR-23b in the brain tissues of APP/PS1 mice aged at different months is significantly decreased in an age-dependent manner (mean±SEM, n=3, fold change >2).

Example 2 Detection of miR-23b Expression in AD Model Cells

Figure 2:
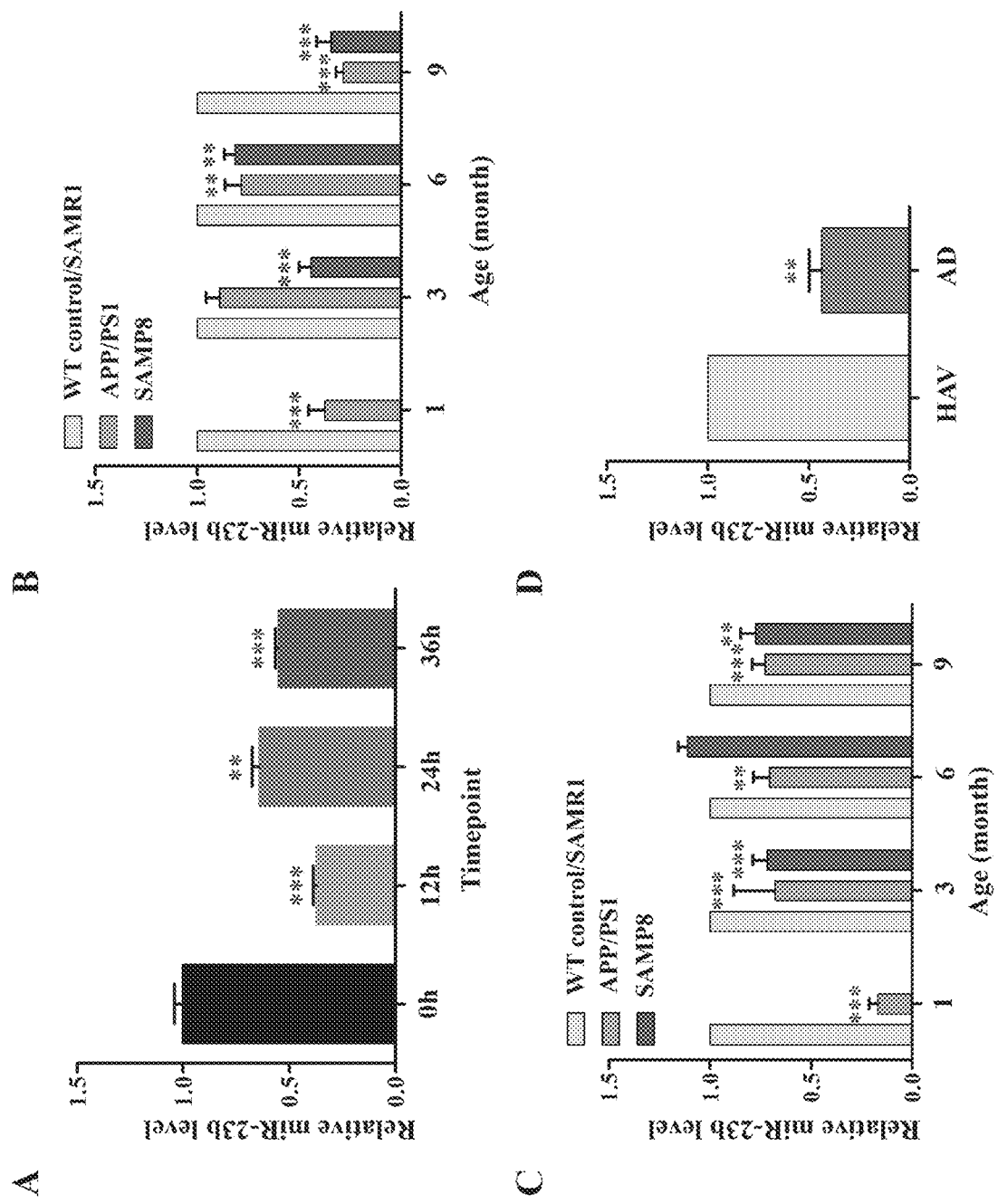
FIG. 2 shows the decreased expression of miR-23b in AD model cells, AD model animals and natural aging animals, and blood of AD patients according to a specific example of the disclosure.

An AD cell model with $Cu^{2+}$-induced damage to APPswe cells was constructed, and the expression change of miR-23b during the pathological process of the AD cell model was detected by the qPCR technology. As shown in A of FIG. 2, compared with the control group (0 h), the expression of miR-23b is significantly reduced at 12 h, 24 h and 36 h after $Cu^{2+}$ damage (mean±SEM, n=3, $p<0.01$, *$p<0.001$).

Example 3 Detection of miR-23b Expression in AD Model Animals and Natural Aging Animals The hippocampal and cortical tissues were collected from 1, 3, 6 and 9-month-old APP/PS1 double-transgenic mice and senescence-accelerated mouse/prone 8 (SAMP8) mice, and the qPCR technology was adopted to detect the expression changes of miR-23b during the pathological process of AD. As shown in B and C of FIG. 2, in the cortical or hippocampal tissues of the two animal models, compared with the control mice (WT control/SAMR1 mice) at the same age, 1, 3, 6, and 9-month-old mice exhibit a significantly-decreased expression level of miR-23b (mean±SEM, n=4, $p<0.01$, *$p<0.001$).

Example 4 Detection of miR-23b Expression in the Blood of AD Patients

The serum of patients who were clinically diagnosed with AD were collected, and the qPCR technology was adopted to detect the miR-23b expression in the serum of the AD patients. As shown in D of FIG. 2, the miR-23b expression in the blood of AD patients is significantly lower than that of healthy volunteers at the same age (mean±SEM, n=5 to 7, **$p<0.01$).

Example 5 Effect of Up-Regulation of miR-23b Expression on Cell Viability

Figure 3:
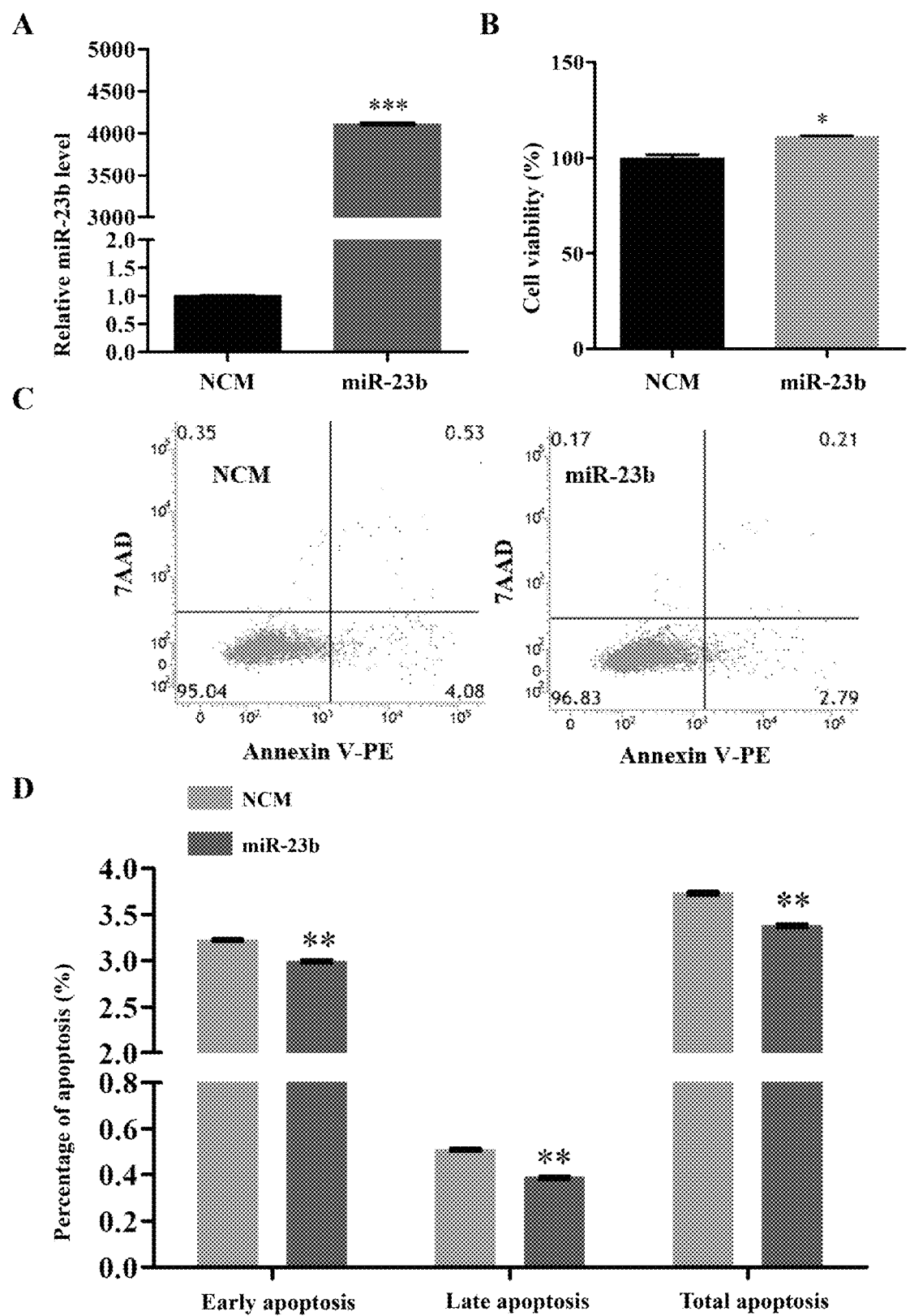
FIG. 3 shows the protective effect of miR-23b on cell viability and apoptosis of neuronal cells in AD model cells according to a specific example of the disclosure.

An in-vitro model with up-regulated miR-23b expression was established by transfecting miR-23b mimics into AD model cells, and the MTS colorimetric method was utilized to detect cell viability. As shown in A and B of FIG. 3, the up-regulation of miR-23b expression alleviates $Cu^{2+}$-induced damage and increases the survival rate of AD model cells (mean±SEM, n=3, *$p<0.05$, ***$p<0.001$).

Example 6 Effect of Up-Regulation of miR-23b Expression on Cell Apoptosis

An in-vitro model with up-regulated miR-23b expression was established by transfecting miRNA mimics into AD model cells, and flow cytometry (FC) was utilized to detect cell apoptosis. As shown in C and D of FIG. 3, the up-regulation of miR-23b expression significantly inhibits early and late apoptosis of neuronal cells ((mean±SEM, n=5, **$p<0.01$).

Figure 4:
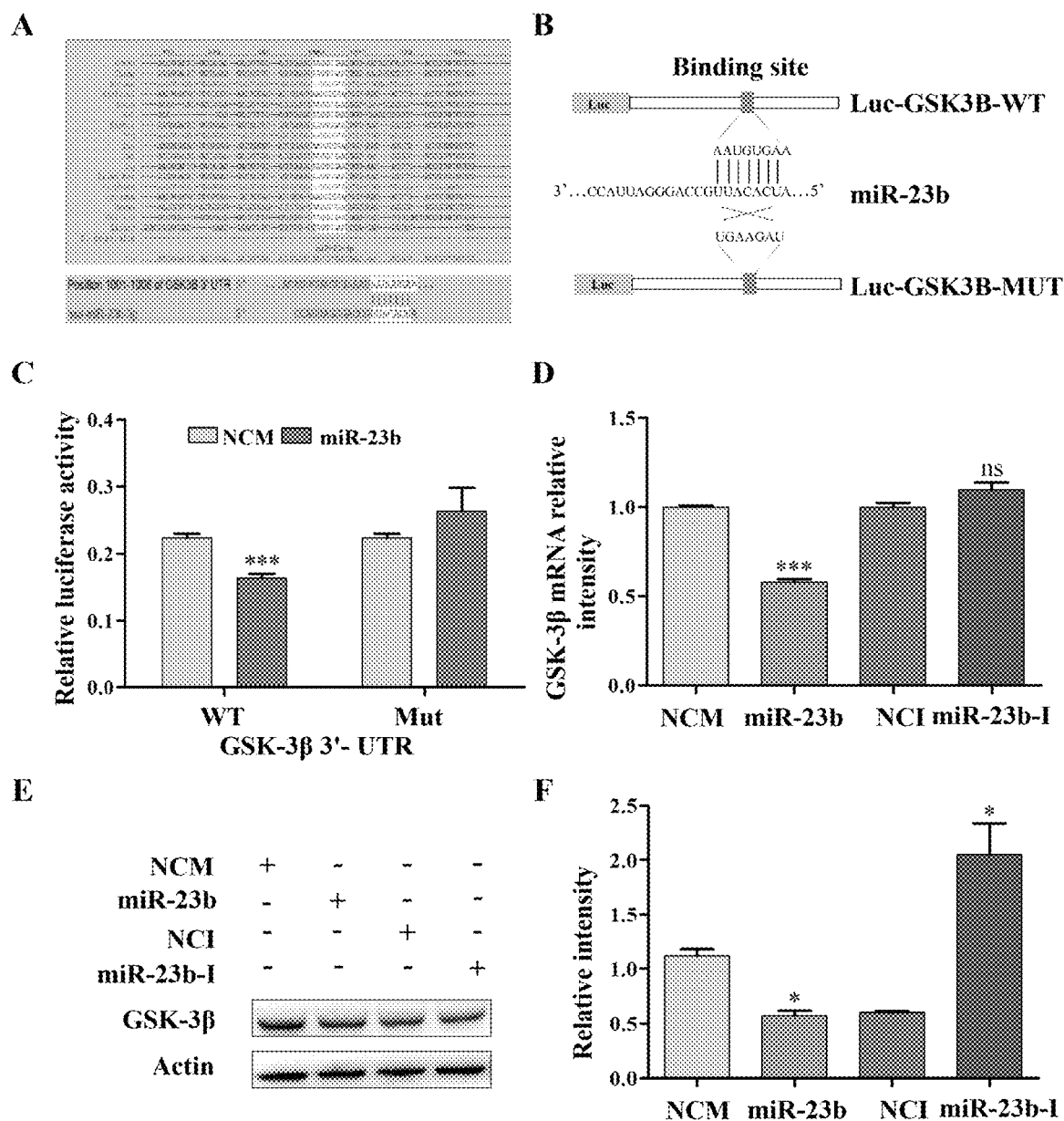
FIG. 4 shows the suppressive effect of miR-23b on the expression of GSK-3β mRNA by specifically targeting GSK3B 3'UTR according to a specific example of the disclosure.

Example 7 Binding of miR-23b to GSK-3β miRNA target gene prediction software (TargetScan and miRanda) was used to predict the binding site of miR-23b with GSK3B, and a fragment of about 150 bp upstream and downstream of the binding site was selected and cloned to the downstream of the luciferase reporter gene to construct a luciferase reporter vector Luc-GSK3B-WT. Based on the principle of changing the base arrangement, a mutant luciferase reporter vector Luc-GSK3B-MUT was constructed, as shown in A and B of FIG. 4. The WT or mutant reporter vector was co-transfected into HEK293 cells with miR-23b mimics. 36 h later, the dual-luciferase reporter gene detection system (Promega) was used to detect the activity of Firefly and *Renilla* luciferase. As shown in C of FIG. 4, after Luc-GSK3B-WT is co-transfected with miR-23b mimics, the up-regulation of miR-23b expression significantly reduces the activity of luciferase. When the binding site is mutated, miR-23b loses its inhibitory effect according to the unchanged luciferase activity (mean±SEM, n=3, ***$p<0.001$).

Example 8 Negative Regulatory Effect of miR-23b on GSK-3β

The in-vitro models with up-regulated or down-regulated miR-23b expression were established by transfecting miRNA mimics/inhibitor into AD model cells. The qPCR technology was utilized to detect the GSK-3β mRNA expression in the cells, and the Western Blot technology was utilized to detect the expression of GSK-3β protein in the cells. As shown in D to F of FIG. 4, the up-regulation of miR-23b expression down-regulates the expression of GSK-3β both at the mRNA and protein levels (mean±SEM, n=3, *$p<0.05$, ***$p<0.001$).

Figure 5:
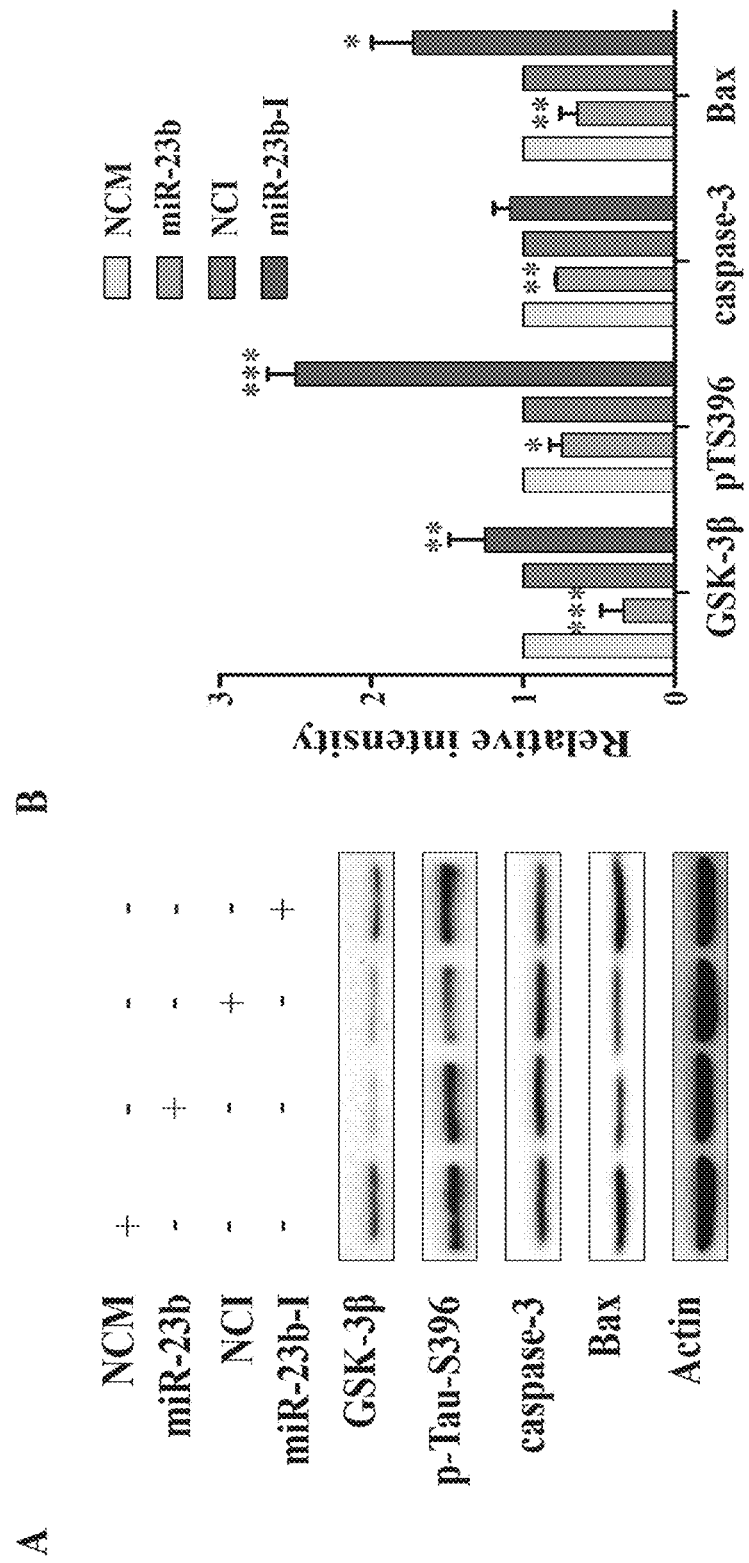
FIG. 5 shows the inhibitory effect of miR-23b on the tau protein phosphorylation levels and recovered effects of miR-23b on the expression of apoptosis-related proteins according to a specific example of the disclosure.

Example 9 Effect of the Up-Regulation or Down-Regulation of miR-23b Expression on the Tau Protein Phosphorylation Level and Apoptosis-Related Protein Expression The in-vitro models with up-regulated or down-regulated miR-23b expression were established by transfecting miRNA mimics/inhibitor into AD model cells, and the Western Blot technology was utilized to detect the phosphorylation of tau protein at Ser396 site and the expression of apoptosis-related proteins Bax and caspase-3. As shown in FIG. 5, compared with the control group (NCM), the miR-23b up-regulation decreases the expression of GSK-3β, the phosphorylation level of tau protein at Ser396 site, and the apoptosis-related proteins Bax and caspase-3. Compared with the control group (NCI), the miR-23b down-regulation increases the expression of GSK-3β, the phosphorylation level of tau protein at Ser396 site, and the expression of apoptosis-related proteins Bax and caspase-3 (mean±SEM, n=6, *$p<0.05$, $p<0.01$, *$p<0.001$).

Figure 6:
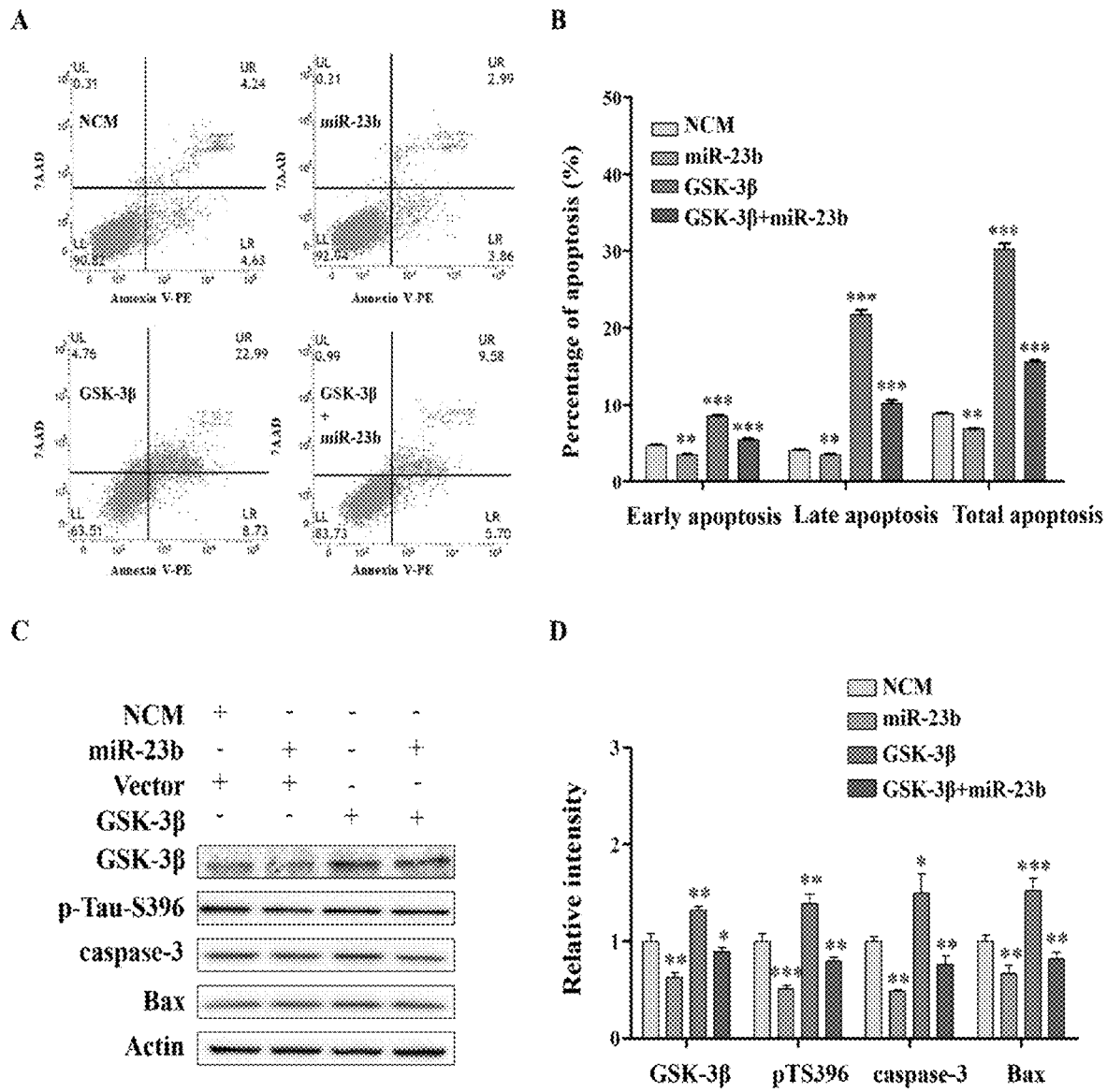
FIG. 6 shows that the suppressive effects of GSK-3β over-expression on miR-23b-mediated tau protein phosphorylation inhibition and neuronal apoptosis reduction according to a specific example of the disclosure.

Example 10 Reversal of GSK-3β Over-Expression on miR-23b-Mediated Inhibtion of Tau Phosphorylation and Neuronal Apoptosis An in-vitro model with up-regulated miR-23b expression was established by transfecting miR-23b mimics into AD model cells, and FC and Western Blot were utilized to detect the apoptosis rate, phosphorylation of tau protein at Ser396 site, and apoptosis-related proteins Bax and caspase-3. Moreover, the over-expression of GSK-3β was achieved by a transfection method, and then the above methods were tested again. As shown in A and B of FIG. 6, the over-expression of GSK-3β significantly increases the apoptosis rate of neuronal cells. As shown in C and D of FIG. 6, the over-expression of GSK-3β also up-regulates the phosphorylation of tau protein at Ser396 site, increases the expression of apoptosis-related proteins Bax and caspase-3, and thus reverses the neuroprotective effect of miR-23b (mean±SEM, n=3 to 6, *p<0.05, p<0.01, *p<0.001).

Figure 7:
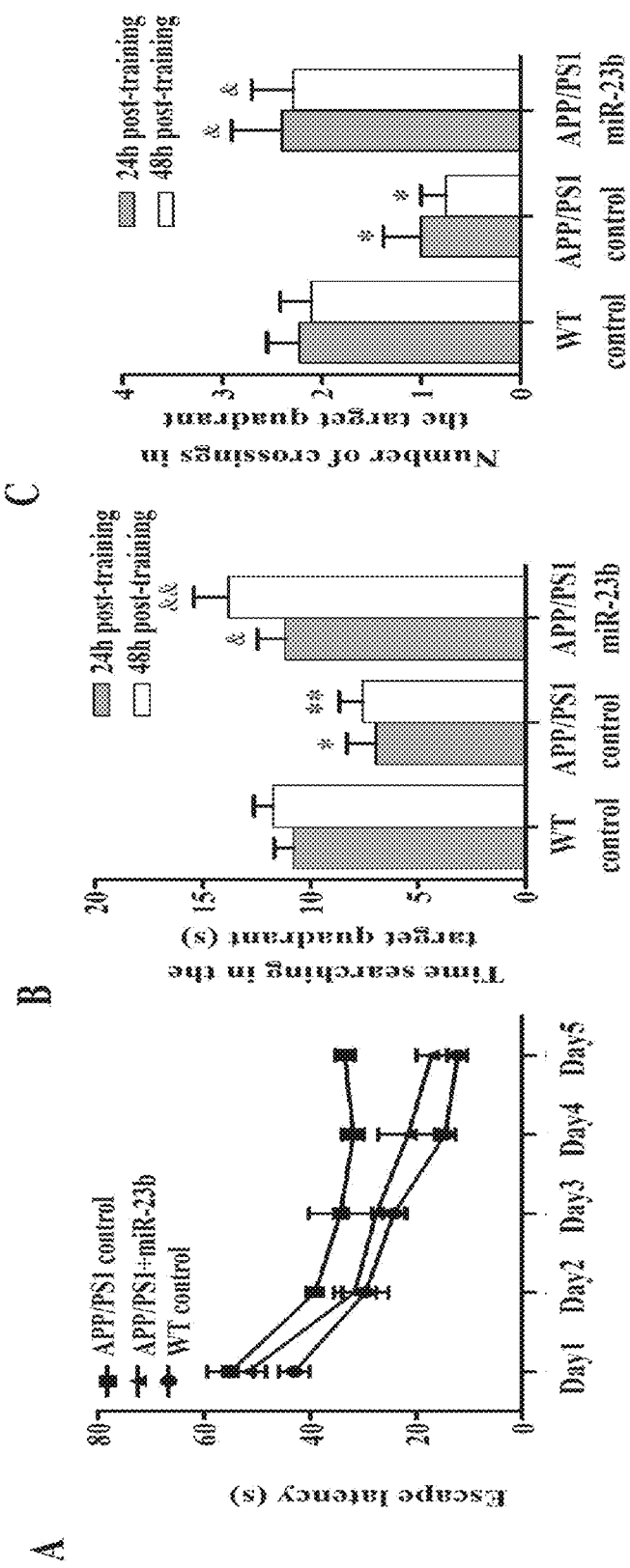
FIG. 7 shows the ameliorative effect of miR-23b on the cognition function of AD model animals according to a specific example of the disclosure.

Example 11 Effect of miR-23b on the Cognitive and Memory Functions of AD Model Animals 6-month-old APP/PS1 mice were selected and intracerebroventricularly injected with miR-23b adeno-associated virus (AAV) and negative control AAV. The Morris water maze test was used to detect the changes in the learning and memory functions of APP/PS1 mice. As shown in FIG. 7, compared with APP/PS1 control mice, the miR-23b-injected APP/PS1 mice exhibit a significantly-shortened latency and a better performance during the five training days. In the space exploration test, the time spent in the platform quadrant and the number of crossings through the platform in the miR-23b-injected APP/PS1 mice are significantly increased (mean±SEM, n=9 to 10, *p<0.05, **p<0.01, &p<0.05, &&p<0.01).

Example 12 Verification of GSK-3β/p-Tau and GSK-3β/Bax/Caspase-3 Pathways Regulated by miR-23b During the Pathological Process of AD In Vivo The hippocampal and cortical tissues were collected from 1, 3, 6, and 9-month-old APP/PS1 double-transgenic mice and 3, 6, and 9-month-old SAMP8 mice, separately. The qPCR technology was utilized to detect the miR-23b expression in the hippocampal and cortical tissues, and the Western Blot technology was adopted to detect the expression level of related proteins in the hippocampal and cortical tissues.

Figure 8:
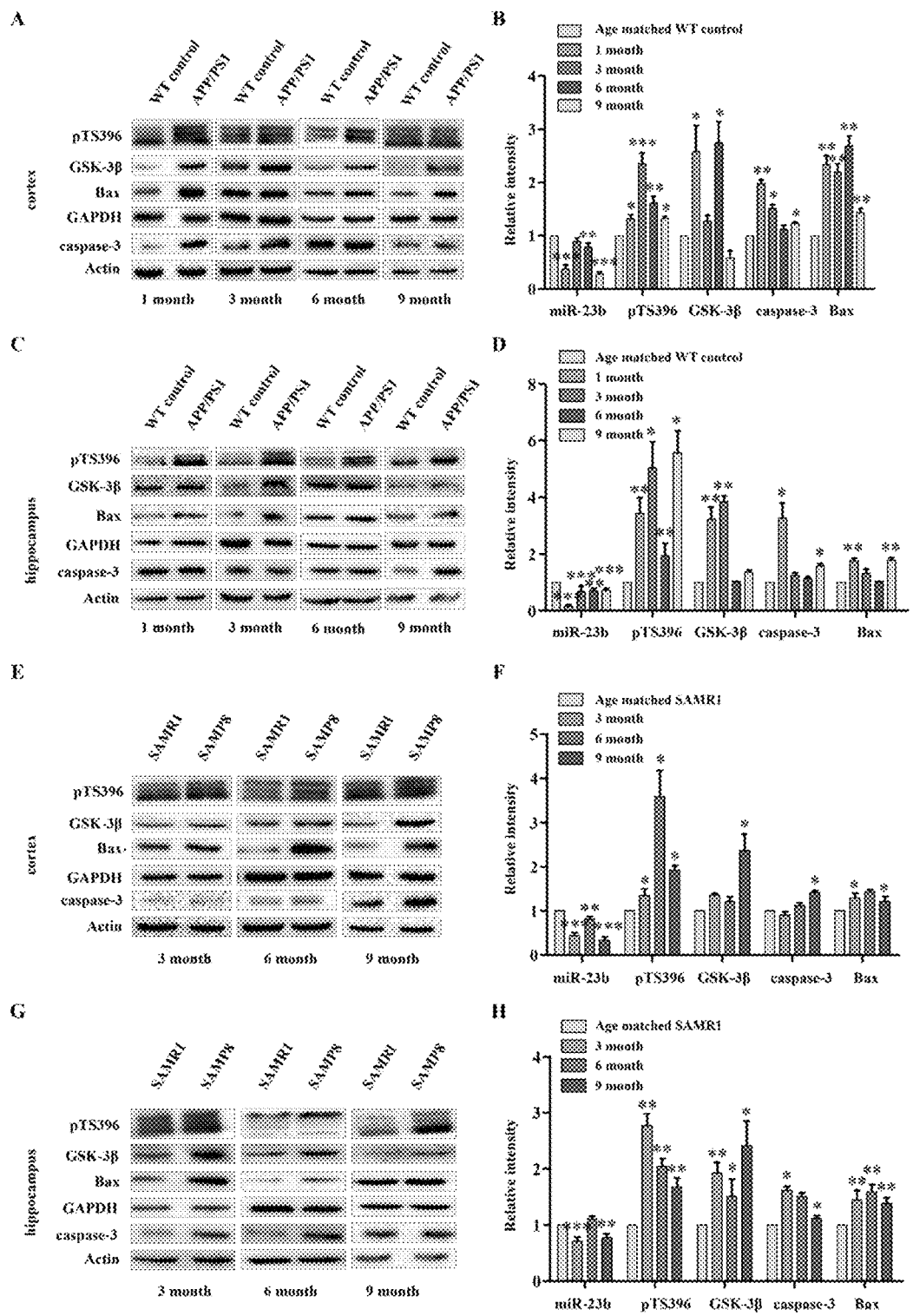
FIG. 8 shows the meliorative effects of miR-23b on GSK-3β/p-tau and GSK-3β/Bax/caspase-3 pathways in AD model animals treated by miR-23b according to a specific example of the disclosure.

As shown in A to D of FIG. 8, the expression level of miR-23b decreases prominently in the cortical and hippocampal tissues of 1, 3, 6, and 9-month-old APP/PS1 double-transgenic mice. Western Blot shows that in the cortical tissues of APP/PS1 double-transgenic mice at different ages, compared with WT mice, the expression of GSK-3β obviously increases, the tau protein phosphorylation level significantly increases, and the expression level of apoptosis-related proteins Bax and caspase-3 remarkably increases in APP/PS1 mice. In the hippocampal tissues, the expression of GSK-3β, p-Tau-S396, caspase-3, and Bax notably increases in APP/PS1 mice from 1 month to 9 months old, as compared to age-matched WT mice (mean±SEM, n=4, *p<0.05, p<0.01, *p<0.001).

As shown in E to H of FIG. 8, the expression level of miR-23b is significantly down-regulated in the cortical tissues of 3, 6, and 9-month-old SAMP8 mice and the hippocampal tissues of 3 and 9-month-old mice. Western Blot shows that in the cortical tissues of SAMP8 mice at different ages, the expression of GSK-3β, the phosphorylation level of tau protein at Ser396 site, and the expression of apoptosis-related proteins Bax and caspase-3 increase notably, especially significant in 9-month-old mice. In the hippocampal tissues, compared with WT mice, the expression of GSK-3β increases significantly, the phosphorylation level of tau protein and the expression of apoptosis-related proteins Bax and caspase-3 increase correspondingly (mean±SEM, n=4, *p<0.05, p<0.01, *p<0.001).

The test results of Examples 1 to 11 of the disclosure show that the expression of the miRNA23 cluster is significantly reduced during the pathological process of AD, which has a function to delay the progression of AD by down-regulating the expression of GSK-3β, inhibiting the phosphorylation of tau protein, and reducing the cell apoptosis of neuronal cells. The miRNA23 cluster is expected to become a new target for the diagnosis and treatment of AD.

Although the disclosure has been described in detail above with general descriptions and specific examples, it will be apparent to those skilled in the art that some modifications or improvements can be made on the basis of the disclosure. Therefore, all these modifications or improvements made without departing from the spirit of the disclosure fall within the scope of the disclosure.

What is claimed is:

1. A method for treating a mouse with Alzheimer's disease (AD), comprising injecting adeno-associated virus (AAV) carrying hsa-miR-23b into the mouse with Alzheimer's disease (AD), wherein the hsa-miR-23b consists of SEQ ID NO: 1.

\* \* \* \* \*

UNITED STATES PATENT AND TRADEMARK OFFICE
CERTIFICATE OF CORRECTION

PATENT NO. : 12,006,551 B1
APPLICATION NO. : 17/865475
DATED : June 11, 2024
INVENTOR(S) : Rui Liu et al.

It is certified that error appears in the above-identified patent and that said Letters Patent is hereby corrected as shown below:

On the Title Page

Item (73) The Assignee is corrected from:
"Institute of Medicinal Biotechnology, Chinese Academy of Medical Sciences and Peking University"

To:
-- Institute of Medicinal Biotechnology, Chinese Academy of Medical Sciences and Peking Union Medical College --

Signed and Sealed this
Tenth Day of September, 2024

Katherine Kelly Vidal
*Director of the United States Patent and Trademark Office*

SEQUENCE LISTING

```
Sequence total quantity: 5
SEQ ID NO: 1            moltype = RNA   length = 97
FEATURE                 Location/Qualifiers
source                  1..97
                        mol_type = other RNA
                        organism = Homo sapiens
SEQUENCE: 1
ctcaggtgct ctggctgctt gggttcctgg catgctgatt tgtgacttaa gattaaaatc   60
acattgccag ggattaccac gcaaccacga ccttggc                           97

SEQ ID NO: 2            moltype = RNA   length = 23
FEATURE                 Location/Qualifiers
source                  1..23
                        mol_type = other RNA
                        organism = Homo sapiens
SEQUENCE: 2
atcacattgc cagggattac cac                                          23

SEQ ID NO: 3            moltype = DNA   length = 50
FEATURE                 Location/Qualifiers
misc_feature            1..50
                        note = reverse transcription primer of hsa-miR-23b-3p
source                  1..50
```

```
                        mol_type = other DNA
                        organism = synthetic construct
SEQUENCE: 3
gtcgtatcca gtgcagggtc cgaggtattc gcactggata cgacgtggta           50

SEQ ID NO: 4            moltype = DNA  length = 19
FEATURE                 Location/Qualifiers
misc_feature            1..19
                        note = qPCR forward primer
source                  1..19
                        mol_type = other DNA
                        organism = synthetic construct
SEQUENCE: 4
cgatcacatt gccagggat                                             19

SEQ ID NO: 5            moltype = DNA  length = 20
FEATURE                 Location/Qualifiers
misc_feature            1..20
                        note = qPCR reverse primer
source                  1..20
                        mol_type = other DNA
                        organism = synthetic construct
SEQUENCE: 5
agtgcagggt ccgaggtatt                                            20
```